United States Patent
Ukegawa et al.

(10) Patent No.: US 8,646,506 B2
(45) Date of Patent: Feb. 11, 2014

(54) APPARATUS FOR MANUFACTURING BODILY EXUDATES ABSORBENT STRUCTURES

(75) Inventors: Kazuo Ukegawa, Kagawa (JP); Akihide Ninomiya, Kagawa (JP)

(73) Assignee: Unicharm Corporation, Ehime (JP)

( * ) Notice: Subject to any disclaimer, the term of this patent is extended or adjusted under 35 U.S.C. 154(b) by 0 days.

(21) Appl. No.: 13/579,981

(22) PCT Filed: Feb. 24, 2011

(86) PCT No.: PCT/JP2011/054178
§ 371 (c)(1),
(2), (4) Date: Oct. 11, 2012

(87) PCT Pub. No.: WO2011/105509
PCT Pub. Date: Sep. 1, 2011

(65) Prior Publication Data
US 2013/0025795 A1    Jan. 31, 2013

(30) Foreign Application Priority Data
Feb. 26, 2010  (JP) .................................. 2010-043183

(51) Int. Cl.
*B32B 37/00*    (2006.01)
(52) U.S. Cl.
USPC ............................ 156/553; 156/581; 156/582
(58) Field of Classification Search
USPC ............... 156/553, 555, 580, 581, 582, 583.1
See application file for complete search history.

(56) References Cited

U.S. PATENT DOCUMENTS

| | | | |
|---|---|---|---|
| 5,149,335 A | | 9/1992 | Kellenberger et al. |
| 5,376,203 A | * | 12/1994 | Syme ............................ 156/209 |
| 5,484,505 A | * | 1/1996 | Isakson et al. ................. 156/470 |
| 5,730,818 A | * | 3/1998 | Isakson ............................ 156/66 |

(Continued)

FOREIGN PATENT DOCUMENTS

| | | |
|---|---|---|
| JP | 2008507384 A | 3/2008 |
| JP | 2008508036 A | 3/2008 |
| JP | 2008508052 A | 3/2008 |
| WO | 2007122525 A1 | 11/2007 |

OTHER PUBLICATIONS

International Search Report and Written Opinion for PCT/JP2011/054178, dated Apr. 12, 2011.

*Primary Examiner* — James Sells
(74) *Attorney, Agent, or Firm* — Lowe Hauptman & Ham LLP

(57) ABSTRACT

An apparatus for manufacturing bodily exudates absorbent structures has a rotating drum to convey a first continuous sheet, a feeding mechanism, a second conveying mechanism to convey a second continuous sheet and a sealing mechanism to join the first and second continuous sheets. The rotating drum is formed on its peripheral surface with depressions, leaving a non-depressed peripheral surface segment. Each of the depressions is formed in a central region with a central through-hole extending through each depression from an outer surface to an inner surface of the rotating drum. Within the rotating drum, a suction mechanism is installed to provide a suction effect directed from the outer surface toward the inner surface of the rotating drum so that the first continuous sheet is formed with a first concave region having been deformed along each depression and a second concave region having been deformed toward the central through-hole.

6 Claims, 7 Drawing Sheets

(56) References Cited

U.S. PATENT DOCUMENTS

| | | | |
|---|---|---|---|
| 6,136,142 A * | 10/2000 | Kitagawa et al. | 156/555 |
| 6,176,286 B1 * | 1/2001 | Kitagawa et al. | 156/555 |
| 7,144,241 B2 * | 12/2006 | Hennessey et al. | 425/363 |
| 2006/0021695 A1 | 2/2006 | Blessing et al. | |
| 2006/0024433 A1 | 2/2006 | Blessing et al. | |
| 2006/0048880 A1 | 3/2006 | Blessing et al. | |
| 2007/0039690 A1 | 2/2007 | Walsh et al. | |
| 2007/0246147 A1 | 10/2007 | Venturino et al. | |
| 2008/0215166 A1 | 9/2008 | Blessing et al. | |
| 2009/0098285 A1 | 4/2009 | Walsh et al. | |
| 2010/0224311 A1 | 9/2010 | Blessing et al. | |

\* cited by examiner

APPARATUS FOR MANUFACTURING BODILY EXUDATES ABSORBENT STRUCTURES

RELATED APPLICATIONS

The present application is a National Phase of International Application Number PCT/JP2011/054178, filed Feb. 24, 2011, and claims priority from Japanese Application Number 2010-043183, filed Feb. 26, 2010.

TECHNICAL FIELD

The present invention relates to apparatuses for manufacturing bodily exudates absorbent structures and, more particularly, to apparatuses for manufacturing bodily exudates absorbent structures including exudates absorbent materials such as superabsorbent polymer particles and/or fluff pulp.

BACKGROUND

Conventionally, it is known to sandwich absorbent polymer particles between a pair of sheets, then to bond these two sheets around aggregates of the particles and thereby to form bodily exudates absorbent structures. For example, JP 2008-508052 A (PTL 1) discloses an apparatus adapted to sandwich absorbent polymer particles between a carrier sheet and a covering sheet and then to bond these carrier and covering sheets to each other. The carrier sheet is supported and conveyed by a conveying means and a peripheral surface of the conveying means which is adapted to support the carrier sheet is formed with depressions. The carrier sheet is deformed to be depressed in accordance with the depressions on the peripheral surface of the conveying means. The particles are fed into these depressions of the carrier sheet so that the particles may be prevented from being scattered about.

CITATION LIST

Patent Literature

{PTL 1} JP 2008-508052 A

SUMMARY

Technical Problem

In the invention disclosed in PTL 1, even when the particles are properly fed into the depressions of the conveying means, the particles are not adequately prevented from being scattered about and there has been a possibility that some of the particles might spill out from the depressions. Should the particles having spilled out from the depressions into bond regions between the carrier sheet and the covering sheet, bond strength between these two sheets will be deteriorated.

An object of the present invention is to provide an apparatus for manufacturing bodily exudates absorbent structures improved so that absorbent discrete materials can be fed to target regions and can be prevented from being fed to the other regions.

Solution to Problem

According to the present invention, there is provided an apparatus for manufacturing bodily exudates absorbent structures having a machine direction and a cross-direction, including a first conveying means serving to convey a first continuous sheet, a feeding means serving to feed a first continuous sheet with absorbent discrete materials, second conveying means serving to convey a second continuous sheet to be laminated on the first continuous sheet having been fed with the absorbent discrete materials, and a sealing means serving to seal the first continuous sheet and the second continuous sheet to each other.

The present invention is characterized in that:

the first conveying means includes: an outer surface on which the first continuous sheet is placed; an inner surface opposite to the outer surface; a plurality of depressions formed on the outer surface and arranged intermittently in the machine direction, a non-depressed peripheral surface segment at least defined between each pair of the adjacent depressions; and at least one through-hole formed in the depression so as to extend through from the outer surface to the inner surface;

the feeding means is adapted to feed the absorbent discrete materials to regions of the first continuous sheet corresponding to each depression intermittently in the machine direction;

a suction means is installed on the side of the inner surface of the first conveying means adapted to provide a suction effect directed from the side of the outer surface to the side of the inner surface; and the sealing means is adapted to seal the first continuous sheet and the second continuous sheet at least at a part of the non-depressed surface segment.

As used herein, the term "absorbent discrete materials" means superabsorbent polymer particles and/or fluff pulp (comminuted pulp), which are conventionally used for absorbing and containing bodily exudates such as urine and menstruation blood in disposable diapers, menstruation pads and other sanitary products.

According to one embodiment of the present invention, the through-holes include at least a central through-hole formed in a central region of each depression.

According to another embodiment of the present invention, the non-depressed surface segment is formed with sealing projections extending toward the sealing means.

According to still another embodiment of the present invention, each depression is formed about the through-holes with supporting walls adapted to support the first continuous sheet.

According to yet another embodiment of the present invention, a plurality of the depressions are formed in the cross direction.

According to further another embodiment of the present invention, the first conveying means is provided in the form of a rotating drum of which a peripheral surface is formed with the depressions and the suction means is installed on the side of the inner surface of the rotating drum.

Advantageous Effects of Invention

According to the present invention, particularly one or more embodiments thereof, the first conveying means has the outer surface on which the first continuous sheet is placed and the inner surface opposite to the outer surface. The suction means is installed on the side of the inner surface of the first conveying means so that the suction means may provide suction effect directed from the side of the outer surface to the inner surface of the first conveying mean. On the outer surface of the first conveying means is formed with depressions which are, in turn, respectively formed with through-holes communicating with the suction means. The first continuous sheet place on the first conveying means is formed with the first concave regions deformed along the respective depressions and second concave regions deformed along the more deeper through-holes under the suction effect provided by the suction means. The absorbent discrete materials poured to the depressions are retained in the second concave regions and, even if the absorbent discrete materials partially scatter about, these discrete materials move back along slant face of the first concave region into the second concave region. Consequentially, the discrete materials should not scatter out from the depression.

DESCRIPTION OF EMBODIMENTS

Figure 1:
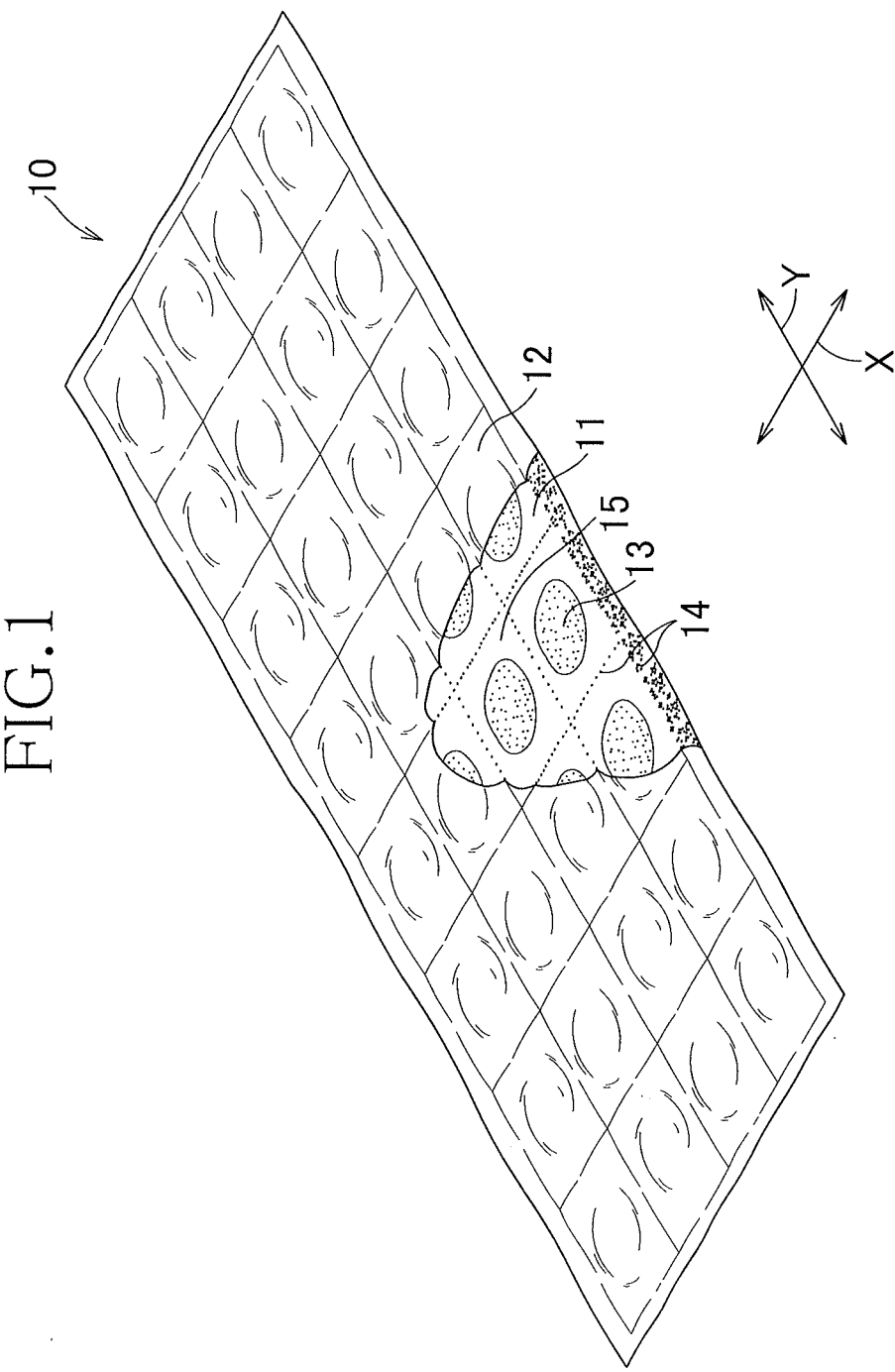
FIG. 1 is a perspective view showing an embodiment of a bodily exudates absorbent structure made by an apparatus for manufacturing bodily exudates absorbent structures according to the present invention.

FIG. 1 exemplarily illustrates a bodily exudates absorbent structure 10 made by an apparatus for manufacturing bodily exudates absorbent structures 1 according to the present invention. The bodily exudates absorbent structure 10 has a longitudinal direction Y and a transverse direction X and includes a first sheet 11, a second sheet 12 and absorbent discrete materials 13 sandwiched between these two sheets 11, 12. Both the first sheet 11 and the second sheet 12 may be formed, for example, of liquid-permeable fibrous nonwoven fabrics. Alternatively, one of the first and second sheets 11, 12 may be formed, for example, of a liquid-impermeable film. As the discrete materials 13, for example, superabsorbent polymer particles and/or fluff pulp (comminuted pulp) may be used.

The first and second sheets 11, 12 are sealed to each other along a plurality of sealing lines 14 extending in the longitudinal direction Y and along a plurality of sealing lines 14 extending in the transverse direction X. The sealing lines 14 extending in the longitudinal and transverse direction Y and X intersect with one another to define a plurality of cells 15 partitioned off one another. The discrete materials 13 are retained within these cells 15.

Such bodily exudates absorbent structure 10 may be used in disposable wearing articles such as diapers, menstruation pads and the like. Specifically, the bodily exudates absorbent structure 10 may be attached to the inner side of the article facing the wearer's body to absorb and to contain bodily exudates such as urine or menstruation blood and thereby to prevent the bodily exudates from leaking out of the article. Even if the discrete materials 13 are eccentrically distributed in each of the cells 15, substantially uniform absorption capacities may be assured over all the entire area of the absorbent structure 10 since these cells 15 are evenly distributed over the whole area of the absorbent structure 10 in the longitudinal direction Y as well as in the transverse direction X.

Figure 2:
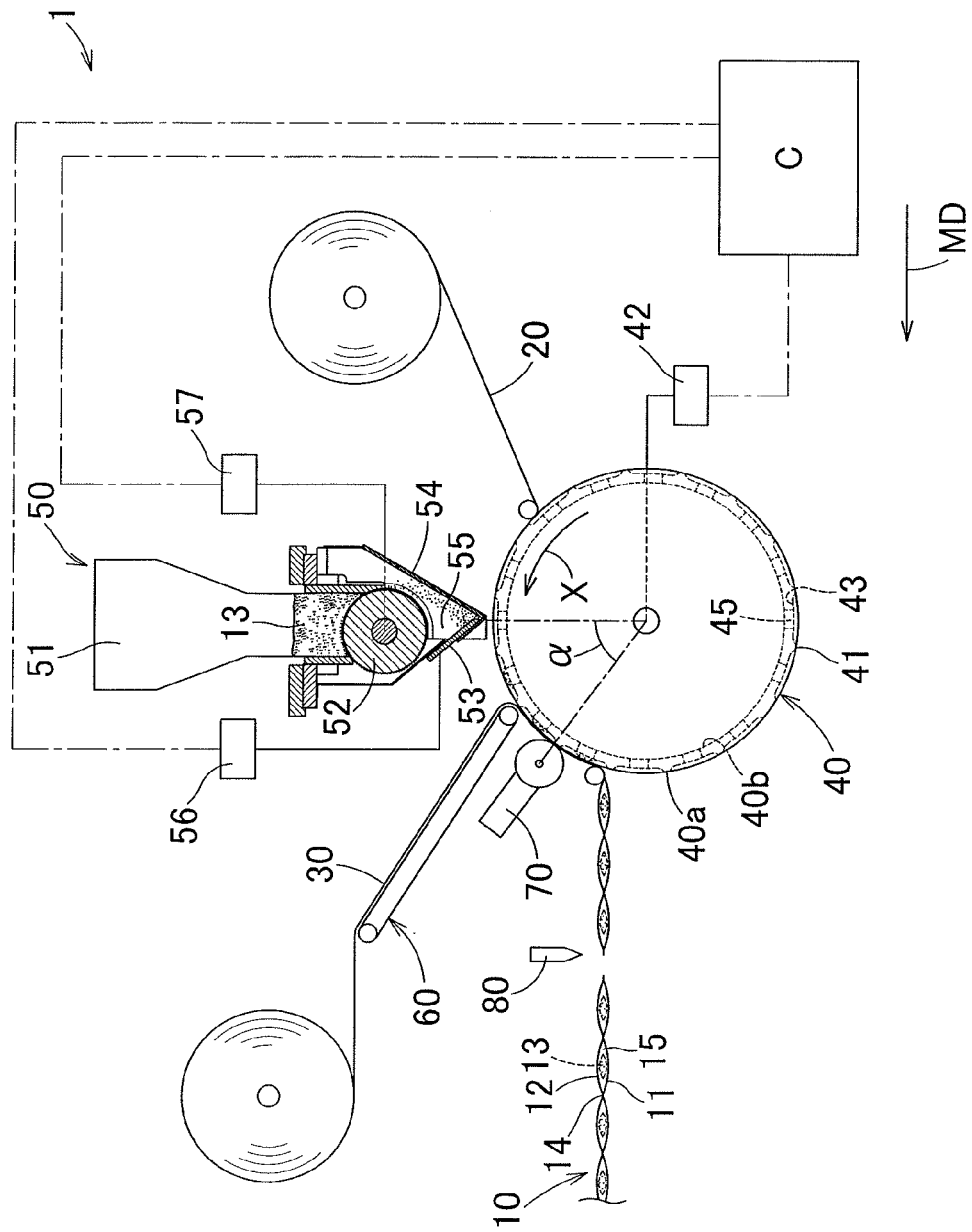
FIG. 2 is a schematic overall view of the apparatus for manufacturing bodily exudates absorbent structures.
Figure 3:
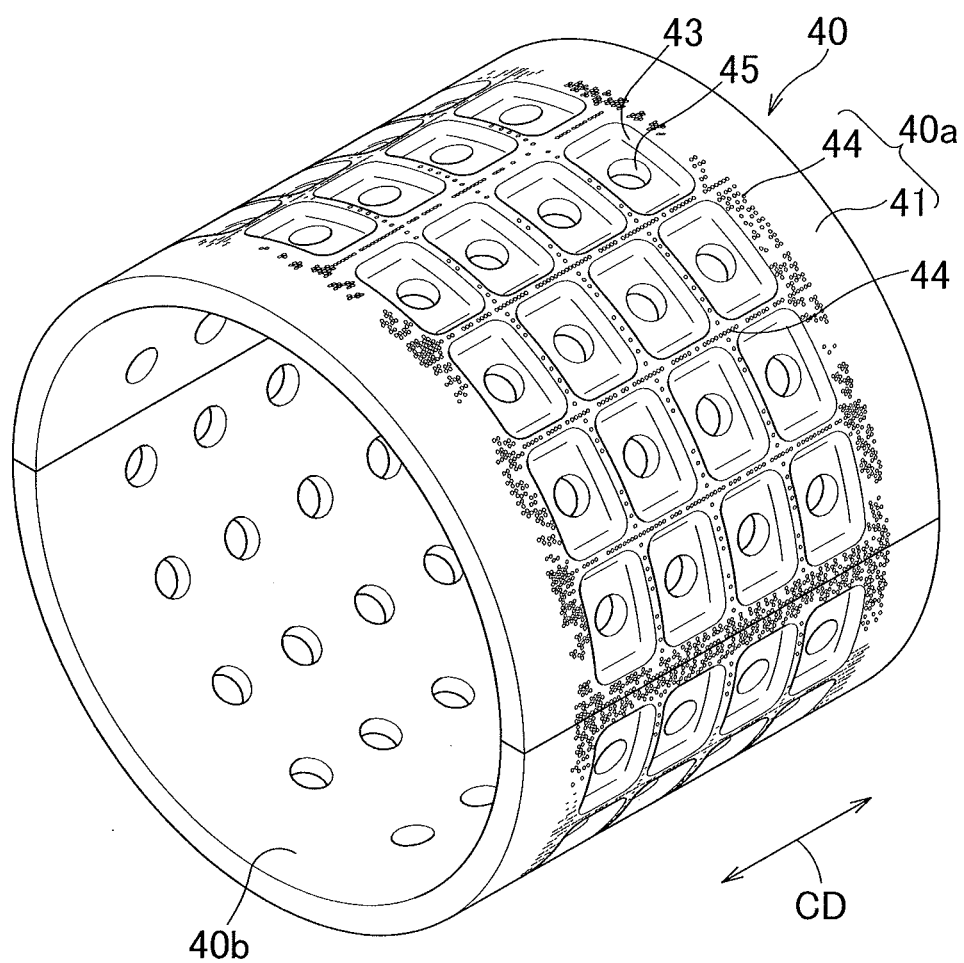
FIG. 3 is a perspective view of a rotating drum.
Figure 4:
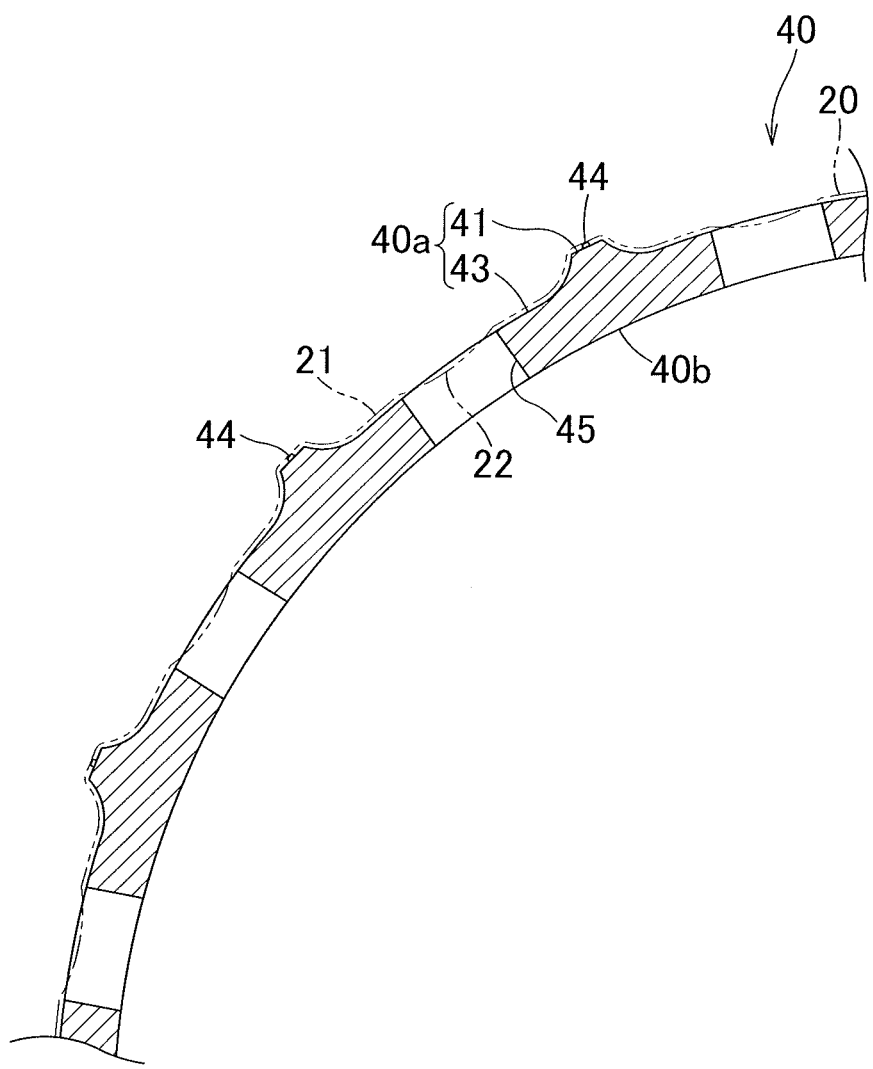
FIG. 4 is a partial sectional view of the rotating drum.
Figure 5:
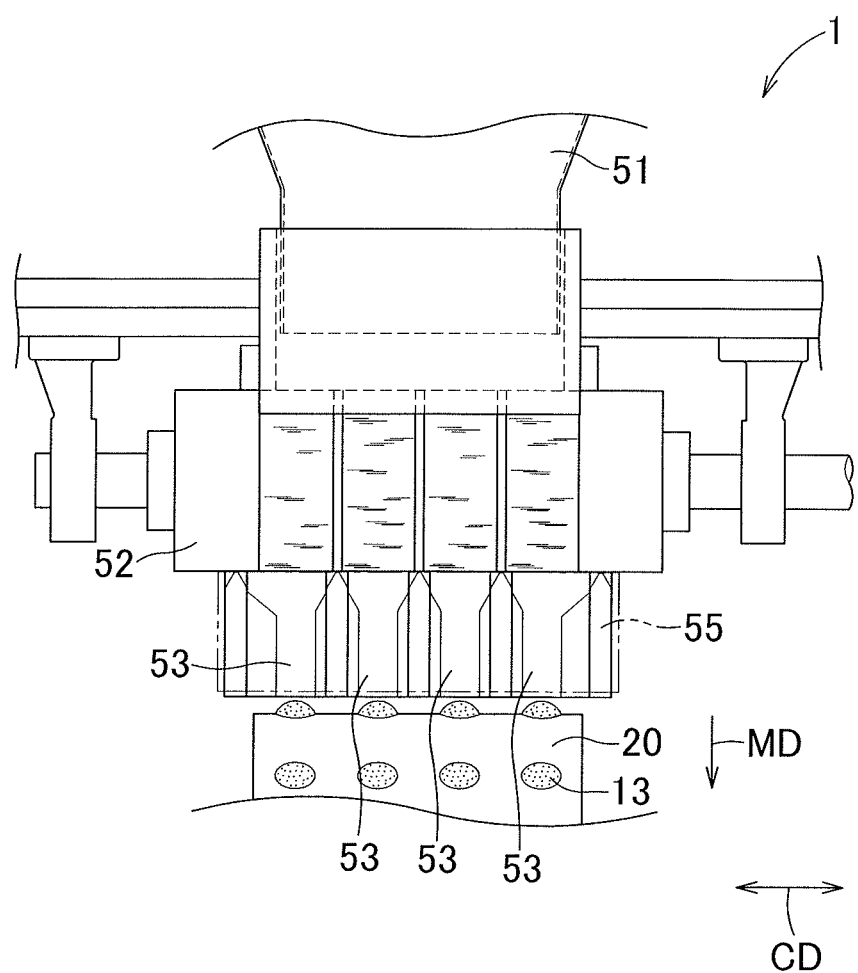
FIG. 5 is a diagram partially illustrating the apparatus for manufacturing bodily exudates absorbent structures.

FIGS. 2 through 5 exemplarily illustrate an apparatus for manufacturing bodily exudates absorbent structures 1. FIG. 2 is a schematic overall view of an apparatus for manufacturing bodily exudates absorbent structures 1, FIG. 3 is a perspective view of a rotating drum 40, FIG. 4 is a partial sectional view of the rotating drum 40 and FIG. 5 is a diagram partially illustrating the apparatus 1.

The apparatus 1 includes a rotating drum 40 as first conveying means serving to convey a first continuous sheet 20, a feeding means 50 serving to feed the first continuous sheet 20 with the discrete materials 13, second conveying means 60 serving to a convey second continuous sheet 30 to be laminated on the first continuous sheet 20 having been fed with the discrete materials 13, and sealing means 70 serving to bond the first and second continuous sheets 20, 30 to each other. A direction in which the first and second continuous sheets 20, 30 are conveyed will be designated herein as a machine direction MD and a direction which is orthogonal to the machine direction MD will be designated as a cross direction CD.

The first and second continuous sheets 20, 30 are prepared in the form of fibrous webs respectively corresponding to the first sheet 11 and the second sheet 12 of the bodily exudates absorbent structure 10. The first and second continuous sheets 20, 30 may be formed of liquid-permeable heat-sealable fibrous nonwoven fabrics containing thermoplastic synthetic resins. For example, spun bonded fibrous nonwoven fabrics containing polypropylene fibers or polyethylene fibers as the heat-sealable fibers may be used. As one of the first and second continuous sheets 20, 30, liquid-impermeable plastic films or the like may be used. It should be noted here that, when the liquid-impermeable plastic films are used, the plastic films should be formed with perforations.

The rotating drum 40 is installed on an assembling station of the apparatus adapted to laminate the sheets and the discrete materials which are components of the bodily exudates absorbent structure. The drum 40 has an annular peripheral wall and is driven by rotary drive means 42 to rotate in a counterclockwise direction as indicated by an arrow X. For example, a servomotor may be used as the rotary drive means 42. The rotary drive means 42 may be electrically connected to a controller C adapted to control various factors such as revolutions thereof.

As exemplarily shown in FIGS. 3 and 4, the rotating drum 40 has an outer surface 40a on which the first continuous sheet 20 is placed and an inner surface 40b opposite to the outer surface 40a. The outer surface 40a is formed with a plurality of depressions 43 arranged intermittently in the circumferential direction as well as in the cross direction CD and a non-depressed surface segment 41 at least defined between each pair of the adjacent depressions 43.

Each of the depressions 43 has a length dimension of about 60 mm in the circumferential direction (i.e., machine direction MD), a length dimension of about 40 mm in the cross direction CD and a depth dimension of about 6 mm as measured from the outer surface. A distance between each pair of the adjacent depressions 43 is about 5 mm. The non-depressed surface segment 41 is formed with a plurality of projections 44 extending outward so as to cooperate with a sealing means 70. Each of the projections 44 has a circular sectional shape, a length dimension of about 0.7 mm as measured from the non-depressed surface segment 41 and a diameter of about 1 mm. These projections 44 serving for sealing are arranged in the circumferential direction (i.e., machine direction MD) as well as in the cross direction CD between each pair of the adjacent depressions 43. These projections 44 are arranged also on both laterals of the drum's peripheral surface in the circumferential direction. Specifically, each of the depressions 43 is substantially surrounded by these projections 44. However, it is not essential to form the projections 44 around all of the depressions 43 but the arrangement of these projections 44 may be appropriately varied depending on various factors such as the intended purpose.

In a central region of each depression 43 defined by a point at which a center line bisecting a dimension of each depression 43 in the circumferential direction (i.e., machine direction MD) intersects with a center line bisecting a dimension of the depression 43 in the cross direction CD, the depression 43 is formed with a central through-hole 45 extending from the outer surface 40a to the inner surface 40b of the rotating drum 40. The central through-hole 45 has a circular cross-sectional shape defined by, for example, a diameter of about 20 mm. As used herein, the term "circular" do not necessarily mean perfect circle but includes "oval". In fact the central through-hole 45 may have even polygonal cross-sectional shape. It is also not essential to position the through-hole 45 accurately in the central region of the depression 43 defined by the cross-point of two central lines but it will be adequate if the through-hole 45 substantially matches the cross-point of two central lines.

On the side of the inner surface 40b of the rotating drum 40, suction means such as a suction box (not shown) is installed so as to suck air from the side of the outer surface 40a to the side of the inner surface 40b. If the first continuous sheet 20 is present on the outer surface 40a, a portion of the first continuous sheet 20 lying just on the central through-hole 45 is sucked so as to be deformed downward in accordance with a configuration of this through-hole 45. Under such sucking effect, the first continuous sheet 20 may be stably conveyed and formed with a first concave region 21 deformed in accordance with each depression 43 and a second further concave region 22 deformed toward each central through-hole 45.

The first continuous sheet 20 formed with the first concave region 21 and the second concave region 22 in this manner is now fed with the discrete materials 13. Referring to FIG. 2, the feeding means 50 includes a hopper 51 within which the discrete materials 13 are stored, a roller 52 adapted to feed the discrete materials 13 downward from the hopper 51 to a plurality of retaining spaces 55 defined between each pair of adjacent partitions of a shutter 53 and feeding chutes 54 for temporary retention of the discrete materials 13 until the material 13 increase to a predetermined quantity. When the shutter 53 is opened by opening-closing actuator means 56, the discrete materials 13 are fed onto the first continuous sheet 20. None of the materials 13 may be fed as long as the shutter 53 is in closed state and the discrete materials 13 may be fed upon opening of the shutter 53. Therefore, opening and closing of the shutter 53 may be controlled to feed the first continuous sheet 20 with the discrete materials 13 in the machine direction MD in an intermittent manner.

Referring to FIG. 5, the shutter 53 of the feeding means 50 has the partitions spaced one from another in the cross direction CD so that the discrete materials 13 may be fed to a plurality of target regions arranged intermittently in the cross direction CD as well as in the machine direction MD and this facilitates it to form a plurality of the depressions respectively filled with the discrete materials 13 and arranged intermittently arranged in the longitudinal direction Y as well as in the transverse direction X. In addition, the discrete materials 13 may be distributed into a plurality of the cells to reduce a quantity of the discrete materials 13 to be fed to the target regions.

The roller 52 is formed on its peripheral surface with a plurality of depressions (not shown) extending in the cross direction CD and arranged in the machine direction MD so that the discrete materials 13 may be retained in these depressions during rotation of the roller 52 until the discrete materials 13 are transferred to the retaining space 55. Size of the respective depressions formed on the peripheral surface of the roller 52 may be appropriately dimensioned to control a quantity of the discrete materials 13 to be transferred. The roller 52 is driven by revolution drive means 57 which is, in turn, electrically connected to the controller C so that various factors such as revolutions thereof may be controlled. The shutter 53 is driven by the opening-closing actuator means 56 which is, in turn, electrically connected to the controller C so that the timing to open or close the shutter 53 may be controlled. In this way, the opening-closing actuator means 56, the revolution drive means 57 for the roller 52 and the revolution drive means 42 for the rotating drum may be synchronized under the control by the controller C to assure that a predetermined quantity of the discrete materials 13 may be fed to the target positions corresponding to the depressions 43 of the rotating drum 40.

As has previously been described, the first continuous sheet 20 is placed on the peripheral surface of the rotating drum 40 and the sheet 20 is formed in the regions of the sheet 20 corresponding to the depressions 43 of the peripheral surface with the first and second concave regions 21, 22. The discrete materials 13 are fed into these concave regions 21, 22. More specifically, the discrete materials 13 are fed so as to get centered on the central region of each depression 43 and thereby it is assured that the discrete materials 13 are poured into the second concave region 22. Even if the discrete materials 13 fed in this manner unintentionally scatter out of the second concave region 22, the discrete materials 13 having scattered out will move back along a slant surface of the first concave region 21 formed around the second concave region 22 into the second concave region 22 which is the deepest region. Therefore, the discrete materials 13, even if partially scatter out of the depression 43, should not remain on the non-depressed peripheral surface segment 41 of the rotating drum 40. In this way, the discrete materials 13 are surely retained within the depression 43.

The central through-hole 45 is a region farthest from the non-depressed peripheral surface segment 41. The discrete materials 13 may be poured into the central through-hole to assure the discrete materials 13 to be kept sufficiently distanced from the non-depressed peripheral surface segment 41. As a result, the discrete materials 13 may be further reliably prevented from being left on the non-depressed initial peripheral surface segment 41.

On the first continuous sheet 20 having been fed with the discrete materials 13, the second continuous sheet 30 conveyed by the second conveying means 60 is laminated and these sheets 20, 30 are bonded to each other by a sealing means 70. The sealing means 70 may be implemented, for example, in the form of a heat roller adapted to press the first continuous sheet 20 and the second continuous sheet 30 on heating against the side of the rotating drum 40. Thereupon, the first and second continuous sheets 20, 30 are successively squeezed and heat-sealed between the sealing projections 44 formed on the peripheral surface of the rotating drum 40 and the sealing means 70 to form the sealing lines 14. The sealing projections 44 are formed around the respective depressions 43 and the portions of the first continuous sheet deformed in according with the respective depressions 43 have been filled with the discrete materials 13. With such an arrangement, the discrete materials 13 may be retained within the respective cells 15 having been sealed by the sealing projections 44. A distance between each pair of the adjacent sealing projections 44 is preferably set to a degree preventing the discrete materials 13 from passing through therebetween. The sealing projections 44 on both laterals on the peripheral surface of the rotating drum 40 have a purpose of securely preventing the discrete materials 13 from scattering out beyond outside them and in view of this, the number of these sealing projections 44 are preferably more than the number of the sealing projections formed in the other regions to enlarge the sealed area.

Referring to FIG. 2, an angle α between a feed throat defined by lower ends of the shutter 53 and the feeding chutes 54 and the sealing means 70 is preferably 90° or less. This is for the reason that, if sealing occurs at a position beyond 90°, the discrete materials 13 having been fed onto the first continuous sheet 20 will spill out.

The first and second continuous sheets 20, 30 having been sealed to each other in this manner may be cut by a cutting means 80 such as a cutter to obtain the bodily exudates absorbent structure 10 as illustrated in FIG. 1. The cutting line is preferably set on the sealed region 14 defined by the sealing projection 44 to prevent the discrete materials 13 from falling off out of the cells 15. According to the present embodiment, the cutting lines are preset so that a pair of the bodily exudates absorbent structures 10 may be formed per one rotation of the rotating drums 40. In the region including the cutting line, two or more rows of the sealing projections 44 are formed to assure sufficiently wide sealed region.

In the apparatus as has been described above, the first continuous sheet 21 is formed with the first concave region 21 and the second concave region 22 so that the discrete materials 13 may be prevented from scattering out of each depression 43. If the discrete materials 13 scatter out of the depression 43, such scattering discrete materials 13 will interfere with sealing between the first and second continuous sheets 20, 30 and deteriorate sealing strength. If the first and second continuous sheets 20, 30 are sealed together with the discrete materials 13 left between these two sheets 20, 30, the superabsorbent polymer particles as the discrete materials 13 will be swollen due to absorption of liquid and sometimes lead to peeling off between the first and second continuous sheets 20, 30 along the sealing lines. If the discrete materials 13 are squeezed between the sealing projections 44 and the sealing means 70, there is a possibility that the heat roller functioning as the sealing means 70 might be abraded. According to the present embodiment, however, the discrete materials 13 may be prevented from scattering out of the depression 43 and thereby the problem as has been described above can be overcome.

While the rotating drum 40 is formed on the non-depressed peripheral surface segment 41 with the sealing projections 44 according to the present embodiment, this is not essential to the present invention. Even if none of the sealing projections 44 is formed, the non-depressed peripheral surface segment 41 is able to come in direct contact with the sealing means 70 and thereby to form the sealed regions therebetween. However, it is preferable to form the sealing projections 44 from the viewpoint that, even if the discrete materials 13 scatter on the non-depressed peripheral surface segment 41, such discrete materials 13 are retained between each pair of the adjacent sealing projections 44 and such discrete materials 13 should not remain on the sealing projections 44. In consequence, the sealing means 70 comes in contact with the sealing projections 44 but not with the discrete materials 13. In this way, the previously described advantageous effects, such as preventive effect against deterioration of the sealing strength and against abrasion of the contact surface may be more reliably assured.

The discrete materials 13 are poured through a plurality of partitioned spaces of shutter 53 arranged in the cross direction CD into the depressions 43 and, in consequence, a quantity of the discrete materials 13 deposited into each depression 43 may be correspondingly reduced in comparison with the case in which a large quantity of the discrete materials 13 are poured at once through a single shutter space into the target region. As a result, scattering of the discrete materials 13 out of the depressions 43 may be prevented more reliably than the above-described case.

Area ratio of the central through-hole to the area of the associated depression 43 is preferably in a range of about 10% to about 60%. If this area ratio is lower than about 10%, it will become difficult to suck the first continuous sheet toward the side of the inner surface of the rotating drum 40 sufficiently to form the second concave region 22 and, even if the second concave region 22 has been formed, there is a possibility that a quantity of the discrete materials 13 to be retained in the second concave region 22 might be unacceptably small. If this area ratio is higher than about 60%, there is possibility that the second concave region 22 defined by the central through-hole 45 and the first concave region 21 defined by the depression 43 could not be distinguished from each other.

The rotating drum 40 has the depressions 43 and the sealing projections 44 formed on its peripheral surface and therefore the depressions 43 and the sealed lines should not be out of the desired relative positional relationship. In consequence, it is assured to form the uniform sized cells 15 in the individual bodily exudates absorbent structure 10 and to retain the discrete materials 13 in the respective cells 15. A commonly used heat roller may be used as the sealing means 70 and it is unnecessary to use a special sealing means having a specified pattern. By using the rotating drum 40 as the first conveying means, the depressions 43 formed on the peripheral surface of the drum 40 may be protected from any deformation. Assuming that flat belt extending in the machine direction MD is used as the first conveying means, there is a possibility that the depressions 43 might be partially abraded due to contact with the sealing means 70. This is because, at an initial stage of contact between the flat belt and the heat roller, an upstream portion of the depression 43 as viewed in the machine direction MD is subjected to a relatively high contact pressure.

Figure 6:
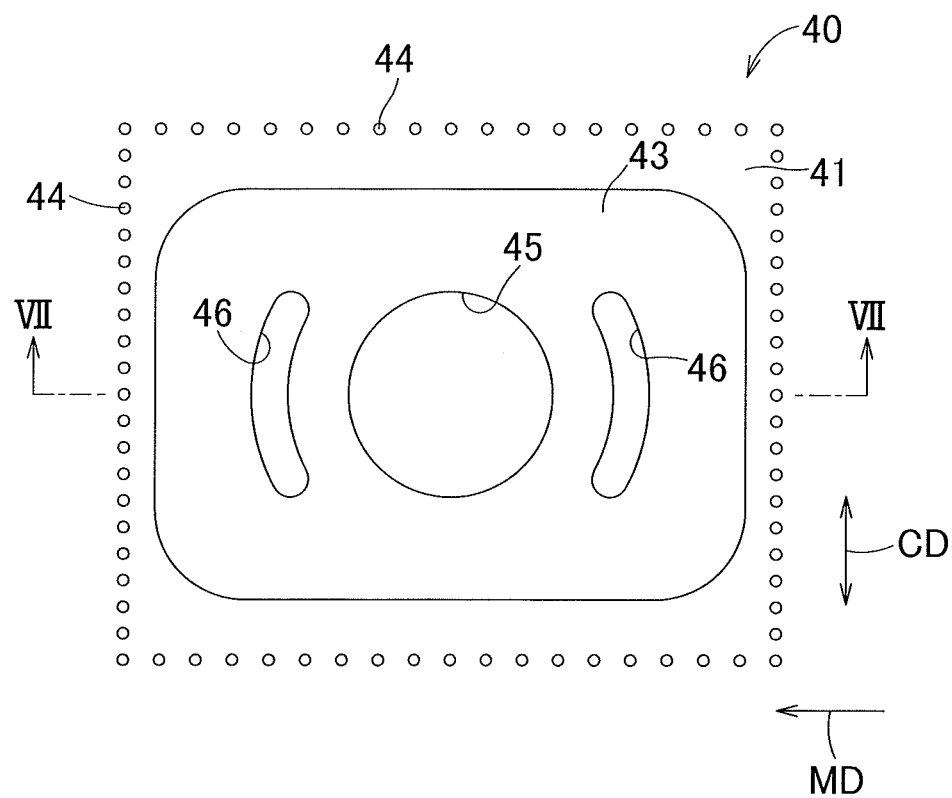
FIG. 6 is a partial plan view of the rotating drum according to another embodiment.
Figure 7:
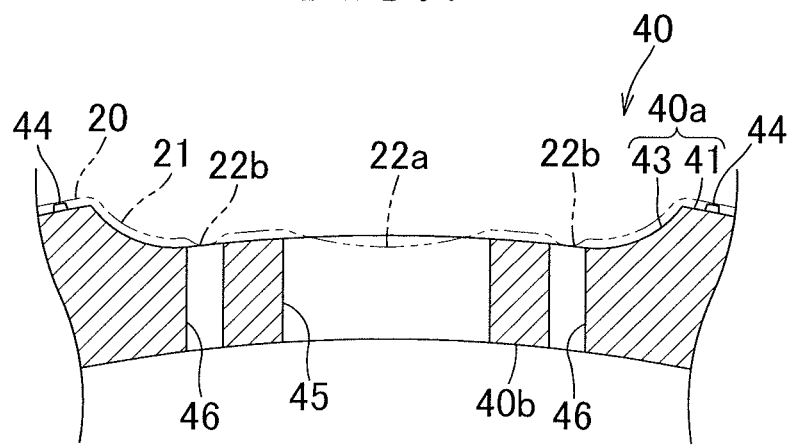
FIG. 7 is a sectional view taken along line VII-VII in FIG. 6.

FIGS. 6 through 9 exemplarily show the depression 43 formed on the peripheral surface of the rotating drum 40 according to other embodiments of the present invention. FIG. 6 is a partial plan view of the rotating drum 40 according one embodiment and FIG. 7 is a sectional view taken along line VII-VII in FIG. 6. As exemplarily shown in FIGS. 6 and 7, the depression 43 may be formed with a plurality of through-holes. Specifically, each depression 43 has a central through-hole 45 formed in a central region as viewed in the machine direction MD as well as in the cross direction CD and lateral through-holes 46 formed on both sides of the central through-hole 45 as viewed in the machine direction as viewed in the machine direction MD.

Referring to FIG. 7, the first continuous sheet 20 is formed with the first concave region 21 deformed along each depression 43, the second concave region 22a deformed corresponding to the central through-hole 45 and second concave regions 22b corresponding to the lateral through-holes 46. A plurality of the second concave regions 22a, 22b defined by the central through-hole 45 and the lateral through-holes 46 serve to improve the preventive effect against scattering of the discrete materials 13.

It is possible to differentiate suction force of the suction means exerted through the central through-hole 45 and through the lateral through-holes 46 on the first continuous sheet. For example, the suction force exerted through the central through-hole 45 may be adjusted to be higher than the suction force exerted through the lateral through-holes 46 to make the second concave region 22a defined by the central concave region 22a deeper than the second concave regions 22b defined by the lateral through-holes 46. In consequence, the discrete materials 13 may be smoothly retained in the central region and thereby scattering out of the discrete materials 13 toward the sealing projections 44 surrounding the central region may be more reliably prevented.

Figure 8:
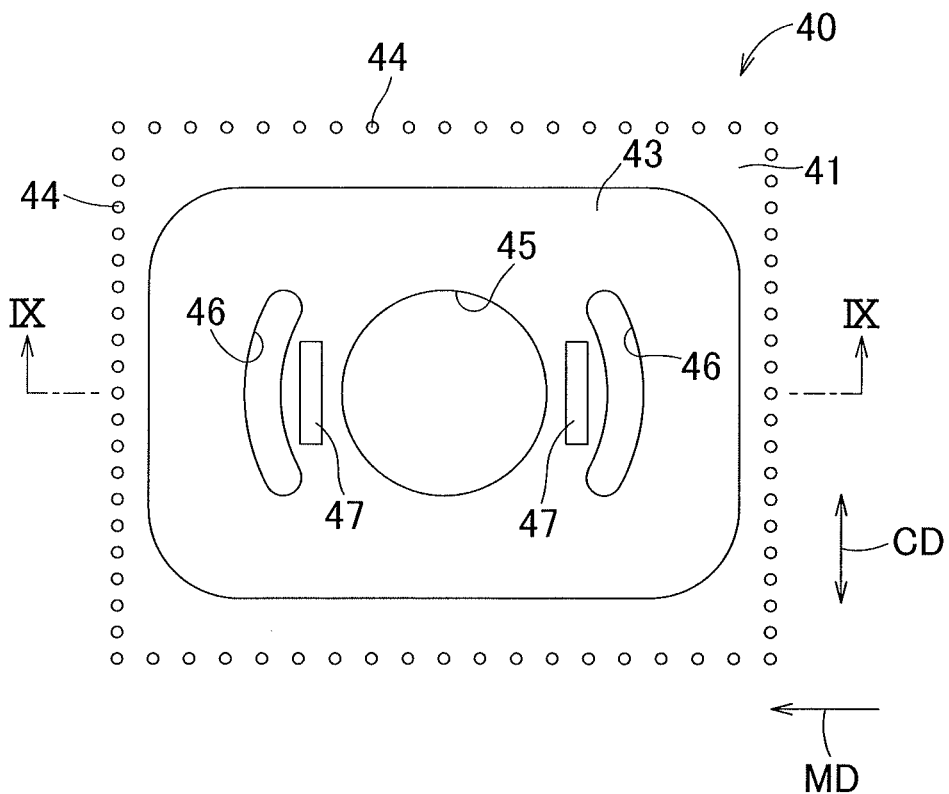
FIG. 8 is a partial plan view of the rotating drum according to still another embodiment.
Figure 9:
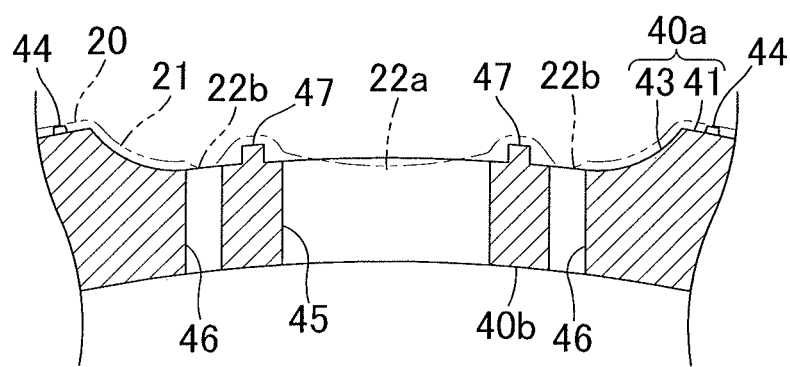
FIG. 9 is a sectional view taken along line IX-IX in FIG. 8.

FIG. 8 is a partial plan view showing the rotating drum 40 according to another embodiment and FIG. 9 is a sectional view taken along line IX-IX in FIG. 8. As exemplarily shown in FIGS. 8 and 9, it is also possible without departing from the scope of the present invention to form supporting walls 47 between the central through-hole 45 and the respective lateral through-holes 46 to support the first continuous sheet 20. The supporting walls 47 allow the second concave region 22a defined by the central through-hole 45 and the second concave regions 22b defined by the lateral through-holes 46 to be made deeper and thereby allow the discrete materials 13 to be smoothly received by the respective concave regions. The supporting walls preferably have a length dimension such that respective upper ends thereof do not extend outward of the depression 43.

While the sealing lines 14 are formed by pressurizing or heating according to the embodiments having been described hereinabove, the present invention is not limited to such technique. For example, it is possible to coat the lines predetermined to form the sealing lines with hot melt adhesives. The feeding means 50 also may be appropriately selected from various types of feeding means as long as adapted for intermittent feeding of the discrete materials 13. Each depression 43 may be formed with a single through-hole 45 or 46 or two or more through-holes 45, 46. The through-hole may be formed in the central region or in the region other than the central region.

While a plurality of the depressions 43 have been described hereinabove so as to be formed so as to be arranged in the machine direction MD as well as in the cross direction CD of the rotating drum 40, the present invention may be implemented in the manner that the peripheral surface of the rotating drum 40 is formed with at least one depression 43 so long as the cross direction CD is concerned. The shape and the respective dimensions of the depression 43 may be appropriately varied.

REFERENCE SIGNS LIST 1 apparatus for manufacturing bodily exudates absorbent structures
10 bodily exudates absorbent structure
13 absorbent discrete materials
20 first continuous sheet
30 second continuous sheet
40 rotating drum (first conveying means)
40a outer surface
40b inner surface
41 non-depressed peripheral surface segment
43 depressions
44 projections cooperating with sealing means
45 central through-holes
46 lateral through-holes
47 supporting walls
50 feeding means
60 second conveying means
70 sealing means
MD machine direction
CD cross direction

The invention claimed is:

1. An apparatus for manufacturing bodily exudates absorbent structures having a machine direction and a cross direction, comprising:
a first conveying means serving to convey a first continuous sheet;
a feeding means serving to feed the first continuous sheet with absorbent discrete materials;
a second conveying means serving to convey a second continuous sheet to be laminated on the first continuous sheet having been fed with the absorbent discrete materials; and
a sealing means serving to bond the first continuous sheet and the second continuous sheet to each other, wherein:
the first conveying means comprises: an outer surface on which the first continuous sheet is placed; an inner surface opposite to the outer surface; a plurality of depressions formed on the outer surface and arranged intermittently in the machine direction; a non-depressed peripheral surface segment at least defined between each pair of adjacent the depressions; and at least one through-hole formed in each depression so as to extend through from the outer surface to the inner surface;
the feeding means is adapted to feed absorbent discrete materials to regions of the first continuous sheet corresponding to each depression intermittently the machine direction;
a suction means is installed on the side of the inner surface of the first conveying means adapted to provide a suction effect directed from the side of the outer surface to the side of the inner surface; and
the sealing means is adapted to join the first continuous sheet and the second continuous sheet at least at a part of the non-depressed surface segment.

2. The apparatus for manufacturing bodily exudates absorbent structures defined by claim 1, wherein the through-holes comprise at least a central through-hole formed in a central region of each depression.

3. The apparatus for manufacturing bodily exudates absorbent structures defined by claim 1, wherein the non-depressed initial surface segment is formed with sealing projections extending toward the sealing means.

4. The apparatus for manufacturing bodily exudates absorbent structures defined by claim 1, wherein the depression is formed about the through-holes with supporting walls adapted to support the first continuous sheet.

5. The apparatus for manufacturing bodily exudates absorbent structures defined by claim 1, wherein a plurality of the depressions are formed in the cross direction.

6. The apparatus for manufacturing bodily exudates absorbent structures defined by claim 1, wherein the first conveying means is provided in the form of a rotating drum of which a peripheral surface is formed with the depressions and the suction means is installed on the side of the inner surface of the rotating drum.

* * * * *